(12) United States Patent
Huang et al.

(10) Patent No.: US 12,357,241 B2
(45) Date of Patent: Jul. 15, 2025

(54) RISK ESTIMATION APPARATUS, RISK ESTIMATION SYSTEM, RISK ESTIMATION METHOD, AND NON-TRANSITORY COMPUTER READABLE RECORDING MEDIUM

(71) Applicant: NEC Corporation, Tokyo (JP)

(72) Inventors: Chenhui Huang, Tokyo (JP); Kenichiro Fukushi, Tokyo (JP); Yusuke Sekiguchi, Sendai (JP); Haruki Yaguchi, Sendai (JP); Keita Honda, Sendai (JP); Shinichi Izumi, Sendai (JP); Dai Owaki, Sendai (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 18/413,446

(22) Filed: Jan. 16, 2024

(65) Prior Publication Data

US 2024/0148337 A1 May 9, 2024

Related U.S. Application Data

(63) Continuation of application No. 17/362,498, filed on Jun. 29, 2021, now Pat. No. 11,925,483.

(30) Foreign Application Priority Data

Jul. 3, 2020 (JP) .................................. 2020-115941

(51) Int. Cl.
*A61B 5/00* (2006.01)
*A61B 5/103* (2006.01)
(Continued)

(52) U.S. Cl.
CPC .......... *A61B 5/7275* (2013.01); *A61B 5/1038* (2013.01); *A61B 5/6807* (2013.01);
(Continued)

(58) Field of Classification Search
CPC ..... A61B 5/1038; A61B 5/112; A61B 5/6807; A61B 2562/0247; A61B 5/7275;
(Continued)

(56) References Cited

U.S. PATENT DOCUMENTS 10,555,689 B1   2/2020  Marquez et al.
11,925,483 B2 *  3/2024  Huang .................. G16H 40/67
(Continued)

FOREIGN PATENT DOCUMENTS

JP   2009-106375 A   5/2009
JP   2016-106973 A   6/2016
WO   2018/164157 A1  9/2018

OTHER PUBLICATIONS

JP Office Communication for JP Application No. 2020-115941, mailed on May 21, 2024 with English Translation.
(Continued)

*Primary Examiner* — Jennifer Robertson
*Assistant Examiner* — Elina Sohyun Jang

(57) ABSTRACT

A risk estimation apparatus includes a data acquisition unit that acquires measured data of foot pressures of the left foot and the right foot obtained by sensors that are provided in shoes and measure the foot pressures, a stance phase identification unit that identifies a starting timing and an ending timing of a stance phase of each of the left foot and the right foot from the measured data of the foot pressures, and a risk estimation unit that estimates a risk of abnormality of a lower limb on the basis of asymmetry between the foot pressures of the left foot and the right foot during the stance phase.

15 Claims, 11 Drawing Sheets

(51) Int. Cl.
    *G16H 40/67* (2018.01)
    *G16H 50/30* (2018.01)

(52) U.S. Cl.
    CPC ............. *G16H 40/67* (2018.01); *G16H 50/30* (2018.01); *A61B 2562/0247* (2013.01); *A61B 2562/04* (2013.01)

(58) Field of Classification Search
    CPC ... A61B 5/1123; A61B 5/4082; A61B 5/1036; A61B 2562/04; G16H 40/67; G16H 50/70; G16H 50/30; G06V 40/25; A43B 3/34; G01G 19/50; G01G 19/52
    See application file for complete search history.

(56) References Cited

U.S. PATENT DOCUMENTS

| | | |
|---|---|---|
| 2009/0240171 A1 | 9/2009 | Morris Bamberg et al. |
| 2014/0195023 A1* | 7/2014 | Statham ............ A63B 69/0028 700/91 |
| 2019/0174862 A1* | 6/2019 | Rakshit ................... A43B 3/38 |
| 2020/0151594 A1* | 5/2020 | Schwartz ............ A61B 5/7267 |

OTHER PUBLICATIONS

JP Office Action for JP Application No. 2020-115941, mailed on Dec. 5, 2023 with English Translation.
Wafal L, Zayegh A, Woulfe J, Aziz SM, Begg R. Identification of Foot Pathologies Based on Plantar Pressure Asymmetry. Sensors (Basel). Aug. 18, 2015;15(8):20392-408. doi: 10.3390/s150820392. PMID: 26295239; PMCID: PMC4570427. (Year: 2015).
Wang C, Kim Y, Shin H, Min SD. Preliminary Clinical Application of Textile Insole Sensor for Herniparetic Gait Pattern Analysis. Sensors (Basel). Sep. 12, 2019;19(18):3950. doi: 10.3390/s19183950. PMID: 31547437; PMCID: PMC6767662. (Year: 2019).

* cited by examiner

| ASYMMETRY | LOWER LIMB ABNORMALITY LEVEL (OSTEOPOROSIS OR THE LIKE) |
|---|---|
| a~b | LEVEL 1 |
| b~c | LEVEL 2 |
| c~d | LEVEL 3 |
| ⋮ | ⋮ |

RISK ESTIMATION APPARATUS, RISK ESTIMATION SYSTEM, RISK ESTIMATION METHOD, AND NON-TRANSITORY COMPUTER READABLE RECORDING MEDIUM

CROSS-REFERENCE TO RELATED APPLICATION

This application is a Continuation of U.S. application Ser. No. 17/362,498, filed Jun. 29, 2021, which is based upon and claims the benefit of priority from Japanese Patent Application No. 2020-115941, filed Jul. 3, 2020, the disclosure of which is incorporated herein in its entirety by reference.

TECHNICAL FIELD

The present invention relates to a risk estimation apparatus, a risk estimation system, a risk estimation method, and a non-transitory computer readable recording medium.

BACKGROUND ART

A technology of providing sensors in shoes and performing evaluation related to the feet has been proposed.

For example, in the system disclosed in PCT International Publication No. WO 2018/164157 (hereinafter referred to as "Patent Document 1"), data obtained using sensors provided in insoles of shoes is stored for each user. In this system, data similar to measured data is selected from stored data, and a likelihood of occurrence of abnormality in the feet, such as the presence or absence of formation of calluses, when a user continuously wears shoes is determined using information that is indicated for the selected data and is related to the feet and the shoes, such as that regarding formation of calluses.

SUMMARY

It is preferable to be able to estimate a risk related to the feet without being limited to a relationship between the feet and shoes.

An example object of the present invention is to provide a risk estimation apparatus, a risk estimation system, a risk estimation method, and a non-transitory computer-readable recording medium capable of resolving the above-described problems.

A first example aspect of the present invention is a risk estimation apparatus including: at least one memory configured to store instructions; and at least one processor configured to execute the instructions to: acquire measured data of foot pressures of a left foot and a right foot obtained by sensors that are provided in shoes and measure the foot pressures; identify a starting timing and an ending timing of a stance phase of each of the left foot and the right foot from the measured data of the foot pressures; and estimate a risk of abnormality of a lower limb on the basis of asymmetry between the foot pressures of the left foot and the right foot during the stance phase.

A second example aspect of the present invention is a risk estimation system including: sensors that are provided in shoes and measure foot pressures of a left foot and a right foot; at least one memory configured to store instructions; and at least one processor configured to execute the instructions to: identify a starting timing and an ending timing of a stance phase of each of the left foot and the right foot from measured data of the foot pressures; and estimate a risk of abnormality of a lower limb on the basis of asymmetry between the foot pressures of the left foot and the right foot during the stance phase.

A third example aspect of the present invention is a risk estimation method including: acquiring, by a risk estimation apparatus, measured data of foot pressures of a left foot and a right foot obtained by sensors that are provided in shoes and measure the foot pressures; identifying, by the risk estimation apparatus, a starting timing and an ending timing of a stance phase of each of the left foot and the right foot from the measured data of the foot pressures; and estimating, by the risk estimation apparatus, a risk of abnormality of a lower limb on the basis of asymmetry between the foot pressures of the left foot and the right foot during the stance phase.

According to the present invention, it is possible to estimate a risk related to the feet other than a relationship between the feet and shoes.

EXAMPLE EMBODIMENT

Hereinafter, example embodiments of the present invention will be described but the following example embodiments do not limit the invention according to the claims. Moreover, not all the combinations of features described in the example embodiments are essential for the solution of the invention.

Figure 1:
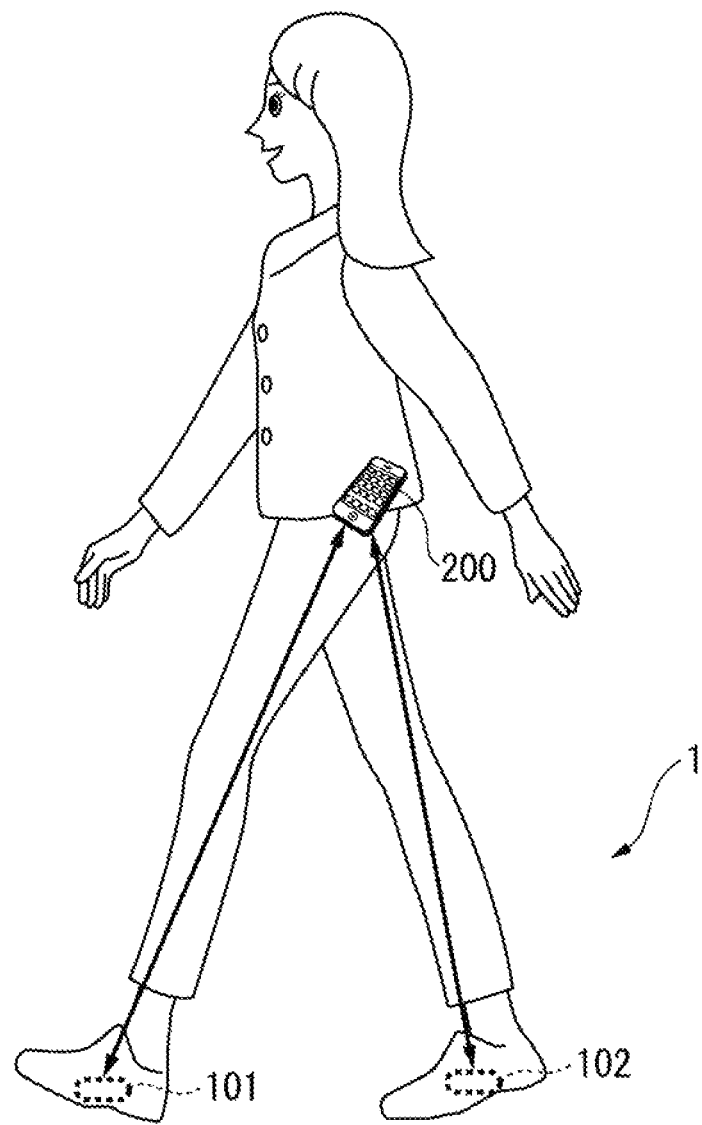
FIG. 1 is a schematic configuration diagram illustrating an example of configurations of apparatuses in a risk estimation system according to an example embodiment.

FIG. 1 is a schematic configuration diagram illustrating an example of a configurations of apparatuses in a risk estimation system according to the example embodiment. In the configuration illustrated in FIG. 1, a risk estimation system 1 includes a left side sensor system 101, a right side sensor system 102, and a risk estimation apparatus 200.

The risk estimation system 1 measures foot pressures of a subject person of risk estimation and estimates a lower limb abnormality risk the subject person of risk estimation on the basis of measured data. Here, foot pressures indicate pressures applied to the soles of the feet. Foot pressures are generated due to the body weight supported by the feet. Here, a lower limb abnormality risk indicates the degree of likelihood of occurrence of abnormality in a lower limb. Moreover, a subject person of risk estimation is also simply referred to as a subject person.

Specifically, the risk estimation system 1 measures foot pressures of the left foot and the right foot when the subject person walks and estimates a lower limb abnormality risk on the basis of asymmetry between the foot pressures of the left foot and the right foot. Here, asymmetry between the foot pressures of the left foot and right foot indicates that the foot pressures during the same phase of walking motion differ between the left foot and the right foot.

Here, if loads applied to the feet are small, bone densities of the feet decrease. If the bone densities of the feet decrease, a lower limb abnormality risk increases. Thus, if loads applied to the feet are small, a lower limb abnormality risk increases.

Hence, the risk estimation system 1 estimates a lower limb abnormality risk on the basis of asymmetry between the foot pressures of the left foot and the right foot. It is thought that the bone density of the foot on a side of a small foot pressure decreases and a lower limb abnormality risk increases due to asymmetry between the foot pressures of the left foot and right foot.

The left side sensor system 101 is provided in a shoe on the left foot side and measures the foot pressure of the left foot. The left side sensor system 101 transmits the measured data of the foot pressure of the left foot to the risk estimation apparatus 200.

The right side sensor system 102 is provided in a shoe on the right foot side and measures the foot pressure of the right foot. The right side sensor system 102 transmits the measured data of the foot pressure of the right foot to the risk estimation apparatus 200.

The left side sensor system 101 and the right side sensor system 102 will be collectively referred to as sensor systems 100. The sensor systems 100 correspond to an example of sensors that are provided in shoes and measure the foot pressures of the left foot and the right foot.

Shoes provided with the sensor systems 100 will be referred to as shoes 810. Of the shoes 810, a shoe for the left foot will be referred to as a left foot shoe 811. The left foot shoe 811 is provided with the left side sensor system 101. Of the shoes 810, a shoe for the right foot will be referred to as a right foot shoe 812. The right foot shoe 812 is provided with the right side sensor system 102.

The risk estimation apparatus 200 estimates a lower limb abnormality risk of the subject person on the basis of asymmetry between the foot pressures of the left foot and the right foot of the subject person. Specifically, the risk estimation apparatus 200 receives the measured data of the foot pressures of the left foot and the right foot from the left side sensor system 101 and the right side sensor system 102. Then, the risk estimation apparatus 200 calculates an index value of asymmetry between the foot pressures of the left foot and the right foot on the basis of the obtained measured data. The risk estimation apparatus 200 calculates a lower limb abnormality risk on the basis of the index value of asymmetry between the foot pressures of the left foot and the right foot.

The risk estimation apparatus 200 is configured using a portable computer such as a smartphone or a tablet personal computer (tablet PC). In this manner, the risk estimation apparatus 200 is configured using a portable computer and the subject person carries the risk estimation apparatus 200, and thus the risk estimation apparatus 200 is continuously positioned near the sensor systems 100. Accordingly, it is relatively easy for the risk estimation apparatus 200 and the sensor systems 100 to communicate with each other, such as in a case in which the risk estimation apparatus 200 and the sensor systems 100 communicate with each other through, for example, short-range wireless communication.

Figure 2:
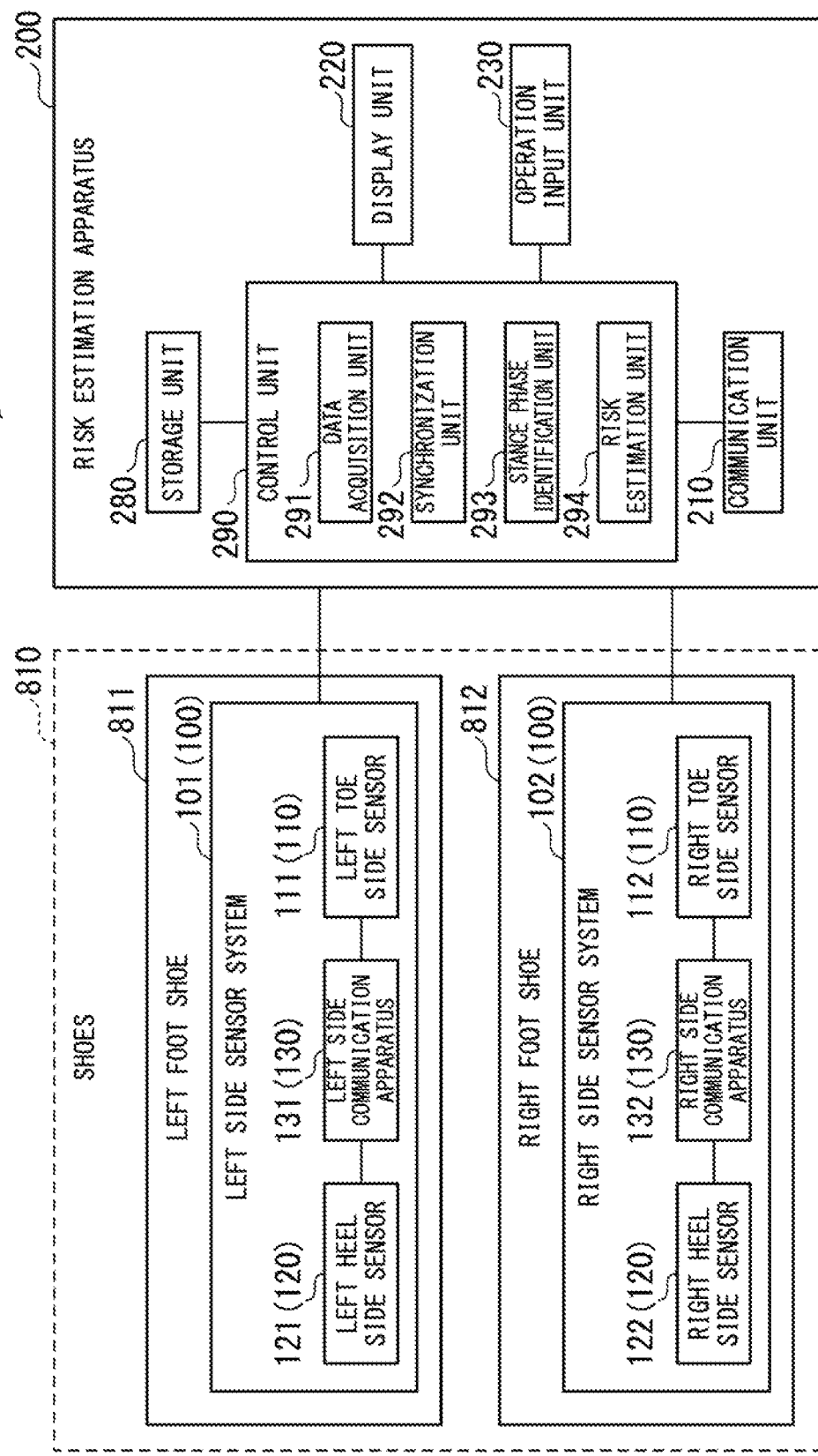
FIG. 2 is a schematic block diagram illustrating an example of a functional configuration of the risk estimation system according to the example embodiment.

FIG. 2 is a schematic block diagram illustrating an example of a functional configuration of the risk estimation system 1. FIG. 2 illustrates a functional configuration of the left side sensor system 101, the right side sensor system 102, and the risk estimation apparatus 200 illustrated in FIG. 1. The left side sensor system 101 includes a left toe side sensor 111, a left heel side sensor 121, and a left side communication apparatus 131. The right side sensor system 102 includes a right toe side sensor 112, a right heel side sensor 122, and a right side communication apparatus 132. The risk estimation apparatus 200 includes a communication unit 210, a display unit 220, an operation input unit 230, a storage unit 280, and a control unit 290. The control unit 290 includes a data acquisition unit 291, a synchronization unit 292, a stance phase identification unit 293, and a risk estimation unit 294.

The left toe side sensor 111 and the right toe side sensor 112 will be collectively referred to as toe side sensors 110. The left heel side sensor 121 and the right heel side sensor 122 will be collectively referred to as heel side sensors 120. The left side communication apparatus 131 and the right side communication apparatus 132 will be collectively referred to as communication apparatuses 130.

The left toe side sensor 111 is provided on the toe side of the left foot shoe 811 and measures the foot pressure on the toe side of the left foot. In particular, the left toe side sensor 111 measures the foot pressure when the toes of the left foot take off the ground.

The left heel side sensor 121 is provided on the heel side of the left foot shoe 811 and measures the foot pressure on the heel side of the left foot. In particular, the left heel side sensor 121 measures the foot pressure when the heel of the left foot contacts the ground. Here, a state in which a foot contacts the ground may be a state in which a shoe contacts the ground. That is, a state in which a shoe contacts the ground may be referred to as a state in which a foot contacts the ground. Moreover, a state in which a foot takes off the ground may be a state in which a shoe takes off the ground. That is, a state in which a shoe takes off the ground may be referred to as a state in which a foot takes off the ground.

The left side communication apparatus 131 transmits the measured data of the left toe side sensor 111 and the left heel side sensor 121 to the risk estimation apparatus 200.

The right toe side sensor 112 is provided on the toe side of the right foot shoe 812 and measures the foot pressure on the toe side of the right foot. In particular, the right toe side sensor 112 measures the foot pressure when the toes of the right foot take off the ground.

The right heel side sensor 122 is provided on the heel side of the right foot shoe 812 and measures the foot pressure on the heel side of the right foot. In particular, the right heel side sensor 122 measures the foot pressure when the heel of the right foot contacts the ground.

The right side communication apparatus 132 transmits the measured data of the right toe side sensor 112 and the right heel side sensor 122 to the risk estimation apparatus 200.

Figure 3:
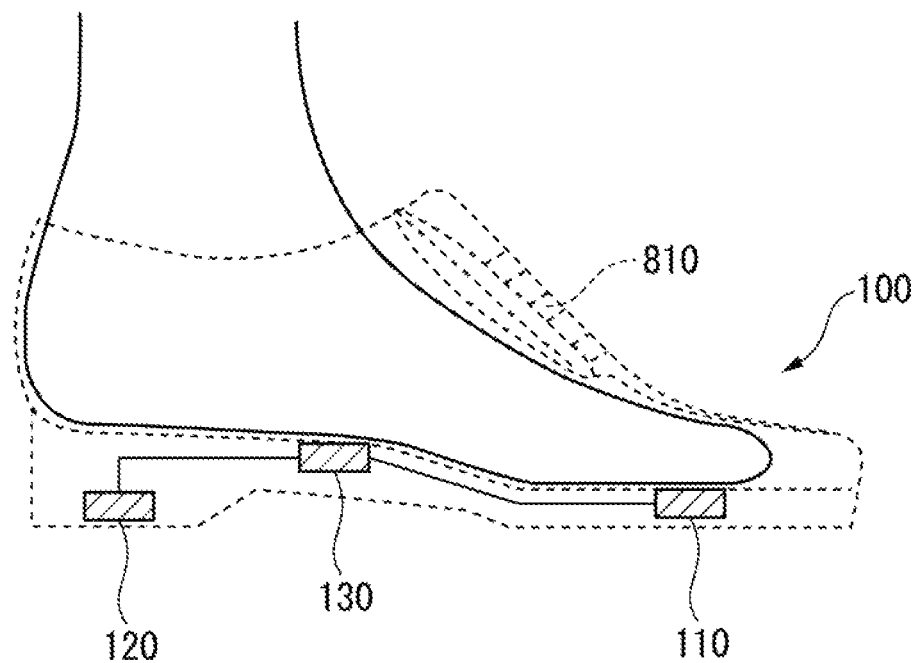
FIG. 3 is a first diagram illustrating an example of disposition of sensors of a sensor system according to the example embodiment.

FIG. 3 is a first diagram illustrating an example of disposition of sensors of the sensor system 100. FIG. 3 illustrates an example of disposition of sensors of the sensor system 100 when the shoe 810 is viewed in a lateral direction.

In the example of FIG. 3, the toe side sensor 110 is provided on the toe side, and the heel side sensor 120 is provided on the heel side. In particular, in the example of FIG. 3, a portion of the shoe 810 that contacts the ground is divided into a toe portion on the toe side (the front side of the shoe 810) and a heel portion on the heel side (the rear side of the shoe 810). The toe side sensor 110 is provided in the toe portion of the shoe 810, and the heel side sensor 120 is provided in the heel portion of the shoe 810.

The communication apparatus 130 is provided between the toe portion and the heel portion of the shoe 810.

It should be noted that FIG. 3 illustrates an example of a case in which the toe side sensor 110 and the heel side sensor 120 are provided in the vicinity of a bottom surface (a surface coming into contact with the ground) of the shoe, but disposition of the toe side sensor 110 and the heel side sensor 120 is not limited thereto. For example, holes for respectively storing the toe side sensor 110 and the heel side sensor 120 may be provided on an upper surface (e.g., immediately below an insole (a shoe insert)) of a shoe sole, and the toe side sensor 110 and the heel side sensor 120 may be respectively fitted into the holes. Alternatively, the toe side sensor 110 and the heel side sensor 120 may be provided in the insole.

Moreover, regarding disposition of the communication apparatus 130, the position of the communication apparatus 130 need only be at a position where measured data can be acquired from the toe side sensor 110 and the heel side sensor 120 and the acquired measured data can be transmitted to the risk estimation apparatus 200.

Figure 4:
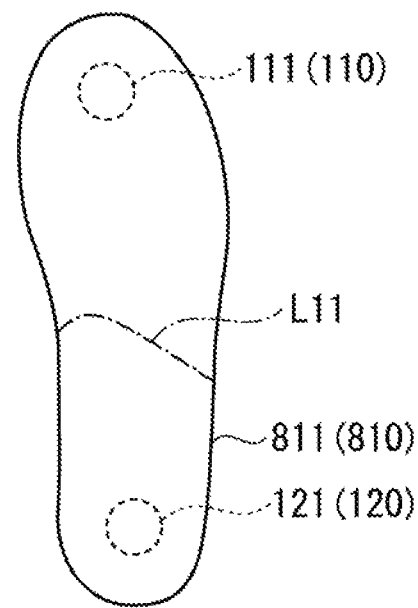
FIG. 4 is a second diagram illustrating an example of disposition of sensors of the sensor system according to the example embodiment.

FIG. 4 is a second diagram illustrating an example of disposition of sensors of the sensor system 100. FIG. 4 illustrates an example of disposition of sensors of the left side sensor system 101 when the left foot shoe 811 is viewed from the shoe sole side. That is, FIG. 4 illustrates an example of disposition of sensors of the left side sensor system 101 when the shoe sole of the left foot shoe 811 is viewed in a manner of being looked up at from the ground side during walking.

In the example of FIG. 4, the left foot shoe 811 is divided into the toe side and the heel side with a line L11 as a boundary. The left toe side sensor 111 is provided on the toe side of the left foot shoe 811. The left heel side sensor 121 is provided on the heel side of the left foot shoe 811.

The right side sensor system 102 may be provided in a bilaterally symmetrical manner with the example of FIG. 4. The right foot shoe 812 is also divided into the toe side and the heel side, the right toe side sensor 112 may be provided on the toe side of the right foot shoe 812, and the right heel side sensor 122 may be provided on the heel side of the right foot shoe 812.

Regarding setting of the toe side and the heel side of the shoe 810, they need only be set such that the toe side sensor 110 is disposed at a position where the foot pressure can be measured when the toes take off the ground and the heel side sensor 120 is disposed at a position where the foot pressure can be measured when the heel contacts the ground.

For example, the toe side and the heel side of the shoe 810 may be set on the basis of the structure of the shoe 810 as in the example of FIG. 3.

Alternatively, the toe side and the heel side of the shoe 810 may be set on the basis of the structure of the foot. For example, with respect to the position of the arch of the sole of the foot when the subject person puts on the shoe 810, the toe side from the arch of the sole of the foot may be set as the toe side of the shoe 810, and the heel side from the arch of the sole of the foot may be set as the heel side of the shoe 810. Alternatively, with respect to a position of the joint portion between the metatarsal bone and the tarsal bone when the subject person puts on the shoe 810, the toe side from the joint portion between the metatarsal and the tarsal bone may be set as the toe side of the shoe 810, and the heel side from the joint portion between the metatarsal bone and the tarsal bone may be set as the heel side of the shoe 810.

The number of sensors included in the sensor system 100 is not limited to two. Depending on a method by which the risk estimation apparatus 200 calculates the index value of asymmetry between the foot pressures of the left foot and the right foot, the sensor system 100 may include only one of the toe side sensor 110 and the heel side sensor 120. That is, a sensor may be provided on only one of the toe side and the heel side of the shoe 810.

Alternatively, the sensor system 100 may include three or more sensors. Alternatively, the sensor system 100 may include one sensor capable of measuring the foot pressures on both the toe side and the heel side.

When the sensor system 100 includes the toe side sensor 110 and the heel side sensor 120, the communication apparatus 130 may transmit each of the measured data of the toe side sensor 110 and the measured data of the heel side sensor 120 to the risk estimation apparatus 200. Alternatively, the communication apparatus 130 may transmit data of foot pressures obtained by summing the foot pressure measured by the toe side sensor 110 and the foot pressure measured by the heel side sensor 120 to the risk estimation apparatus 200.

The communication unit 210 of the risk estimation apparatus 200 communicates with other apparatuses. In particular, the communication unit 210 communicates with the left side communication apparatus 131 and acquires the measured data of the foot pressure of the left foot. Moreover, the communication unit 210 communicates with the right side communication apparatus 132 and acquires the measured data of the foot pressure of the right foot.

The communication scheme of the risk estimation apparatus 200 is not limited to a particular scheme. For example, the risk estimation apparatus 200 may communicate with each of the left side communication apparatus 131 and the right side communication apparatus 132 by means of a communication scheme of short-range wireless communication, but it is not limited thereto.

For example, the display unit 220 includes a display screen such as a liquid crystal panel or a light emitting diode (LED) panel and displays various images. For example, the display unit 220 displays estimation results of a lower limb abnormality risk of the subject person.

However, a method by which the risk estimation apparatus 200 outputs data is not limited to the method in which the display unit 220 displays data. For example, the communication unit 210 may transmit estimation results of a lower limb abnormality risk of the subject person to other apparatuses such as a server apparatus.

For example, the operation input unit 230 includes an input device such as a touch sensor that configures a touch panel provided in the display screen of the display unit 220 and receives an operation of a user. For example, the operation input unit 230 receives an operation of a user instructing estimation of a lower limb abnormality risk.

The storage unit 280 stores various pieces of data. The storage unit 280 is configured using a storage device included in the risk estimation apparatus 200.

The control unit 290 performs various kinds of processing by controlling each unit of the risk estimation apparatus 200. For example, the functions of the control unit 290 are executed by a central processing unit (CPU) included in the risk estimation apparatus 200 reading a program from the storage unit 280 and executing the program.

The data acquisition unit 291 acquires the measured data of the foot pressure of the left foot obtained by the left side sensor system 101 and the measured data of the foot pressure of the right foot obtained by the right side sensor system 102. Specifically, the data acquisition unit 291 extracts the measured data of the foot pressure of the left foot from a reception signal that is a signal received by the communication unit 210 from the left side sensor system 101. Moreover, the data acquisition unit 291 extracts the measured data of the foot pressure of the right foot from a reception signal that is a signal received by the communication unit 210 from the right side sensor system 102.

The data acquisition unit 291 may acquire the measured data of the foot pressures on the heel side and the toe side of each of the left foot and the right foot. For example, the data acquisition unit 291 may acquire the measured data of the toe side sensor 110 and the measured data of the heel side sensor 120. Alternatively, the data acquisition unit 291 may acquire data obtained by summing a measured value of the foot pressure by the toe side sensor 110 and a measured value of the foot pressure by the heel side sensor 120.

The synchronization unit 292 synchronizes the measured data of the foot pressure of the left foot with the measured data of the foot pressure of the right foot. Here, synchronizing the measured data of the foot pressure of the left foot with the measured data of the foot pressure of the right foot indicates associating the measured data of the foot pressure of the left foot with the measured data of the foot pressure of the right foot with respect to at least parts of measurement periods that temporally overlap each other. For example, synchronizing the measured data of the foot pressure of the left foot with the measured data of the foot pressure of the right foot may be associating data for one walking cycle of the left foot with data for one walking cycle of the right foot with respect to parts of measurement periods that overlap each other.

The stance phase identification unit 293 identifies a starting timing and an ending timing of a stance phase of each of the left foot and the right foot from the measured data of the foot pressure of each of the left foot and the right foot.

Figure 5:
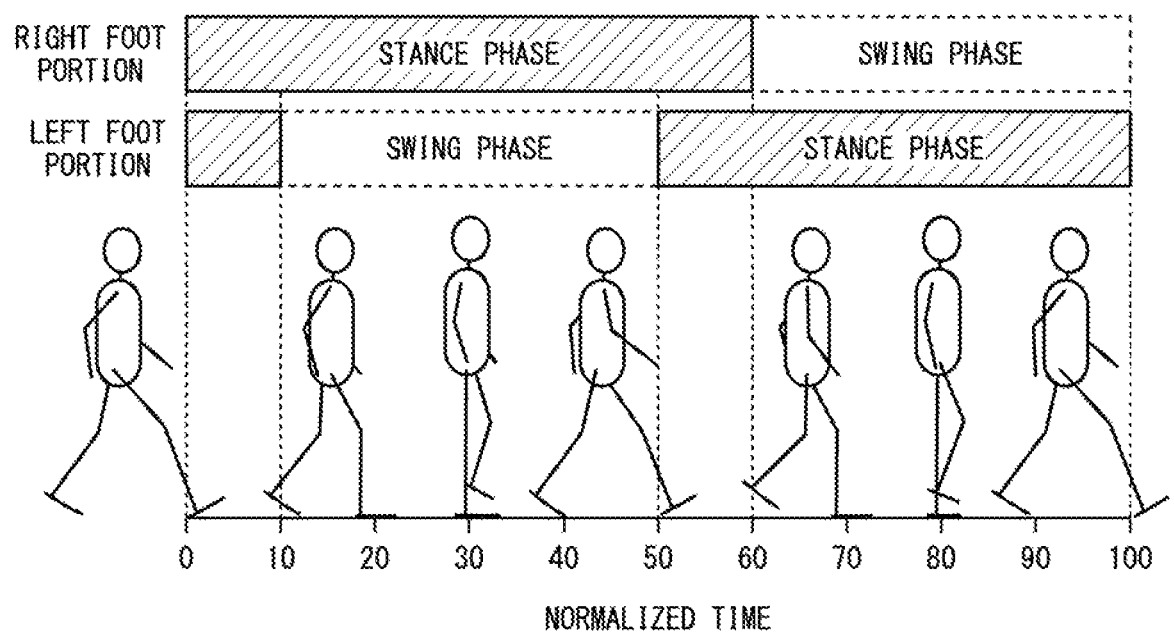
FIG. 5 is a diagram illustrating an example of a stance phase and a swing phase in one walking cycle.

FIG. 5 is a diagram illustrating an example of a stance phase and a swing phase in one walking cycle. The horizontal axis in FIG. 5 indicates times. The horizontal axis in FIG. 5 indicates times in which one walking cycle is normalized to 100.

In the example of FIG. 5, the right foot (the right foot portion) contacts the ground at a normalized time 0, the right foot takes off the ground at a normalized time 60, and the right foot contacts the ground again at a normalized time 100. In the example of FIG. 5, when the foot contacts the ground, the foot contacts the ground from the heel. Moreover, when the foot takes off the ground, the toes take off the ground last. For this reason, the heel of the right foot contacts the ground at the normalized time 0, and the toes of the right foot take off the ground at the normalized time 60. The heel of the right foot contacts the ground again at the normalized time 100.

In this manner, the foot contacts the ground from the heel during ordinary walking, and the toes take off the ground last when the foot takes off the ground.

A period from when the foot contacts the ground until the foot takes off the ground will be referred to as a stance phase. Moreover, a period from when the foot takes off the ground until the foot contacts the ground will be referred to as a swing phase. In the example of FIG. 5, the period from the normalized time 0 to the normalized time 60 corresponds to the stance phase of the right foot. The period from the normalized time 60 to the normalized time 100 corresponds to the swing phase of the right foot.

Regarding the left foot (the left foot portion), the left foot takes off the ground at a normalized time 10, and the left foot contacts the ground at a normalized time 50. Each of the period to the normalized time 10 and the period from the normalized time 50 corresponds to the stance phase of the left foot. The period from the normalized time 10 to the normalized time 50 corresponds to the swing phase of the left foot. Regarding also the left foot, the foot contacts the ground from the heel, and the toes take off the ground last.

In the example of FIG. 5, one walking cycle is a period from when the right foot contacts the ground until the right foot contacts the ground next. However, one walking cycle is not limited thereto and need only be a period from a certain phase in either the left or right foot to the next same phase in the same foot. For example, one walking cycle may be a period from when the left foot contacts the ground until the left foot contacts the ground again next. Alternatively, one walking cycle may be a period from when the right foot takes off the ground until the right foot takes off the ground again next.

In the example of FIG. 5, in the period from the normalized time 0 to the normalized time 60, which is the stance phase of the right foot, and the period from the normalized time 50, which is the stance phase of the left foot, the periods from the normalized time 50 to the normalized time 60 temporally overlap each other. In this manner, parts of the stance phase of the right foot and the stance phase of the left foot overlap each other during walking.

For example, the synchronization unit 292 associates pieces of the measured data in which at least parts of the measurement periods thereof overlap with each other; for example, associates the measured data of the foot pressure of the right foot during the period from the normalized time 0 to the normalized time 60, which is the stance phase of the right foot, with the measured data of the foot pressure of the left foot during the period from the normalized time 50, which is the stance phase of the left foot.

Assuming a case in which a measurement time of the measured data of the foot pressure of the left foot significantly differs from a measurement time of the measured data of the foot pressure of the right foot, it is conceivable that a walking mode at a time of measuring the foot pressure of the left foot differs from a walking mode at a time of measuring the foot pressure of the right foot, for example, a walking speed and a step length differ. Although the foot pressures of the left foot and the right foot are originally symmetrical, for example, the foot pressure of the left foot is substantially similar to the foot pressure of the right foot at the time of measuring the foot pressure of the left foot, there is a likelihood that the risk estimation apparatus 200 may erroneously determine that there is large asymmetry between the foot pressures in the left foot and the right foot because a measuring time of the foot pressure of the left foot differs from a measuring time of the foot pressure of the right foot and the walking modes differ.

In contrast, it is expected that the risk estimation apparatus 200 can determine asymmetry between the foot pressures with higher accuracy by determining asymmetry using associated data of the foot pressures of the left foot and the right foot (data of the foot pressures synchronized by the synchronization unit 292).

The risk estimation unit 294 estimates a lower limb abnormality risk on the basis of asymmetry between the foot pressures of the left foot and the right foot during the stance phase.

For example, the risk estimation unit 294 may estimate a lower limb abnormality risk on the basis of asymmetry between the sum of the foot pressures in the heels of the left foot and the right foot during the stance phase and the sum of the foot pressures in the toes of the left foot and the right foot during the stance phase. That is, the risk estimation unit 294 may estimate a lower limb abnormality risk on the basis of asymmetry between the sum of the foot pressure in the heel and the foot pressure in the toes of the left foot during the stance phase of the left foot and the sum of the foot pressure in the heel and the foot pressure in the toes of the right foot during the stance phase of the right foot.

Moreover, for example, the risk estimation unit 294 may estimate a lower limb abnormality risk on the basis of asymmetry between the foot pressures of the left foot and the right foot during the stance phases of the left foot and the right foot in which parts of the measurement periods temporally overlap each other. That is, the risk estimation unit 294 may determine asymmetry between the foot pressures of the left foot and the right foot using the measured data of the foot pressure of the left foot during the stance phase of the left foot and the measured data of the foot pressure of the right foot during the stance phase of the right foot which are synchronized by the synchronization unit 292.

Figure 6:
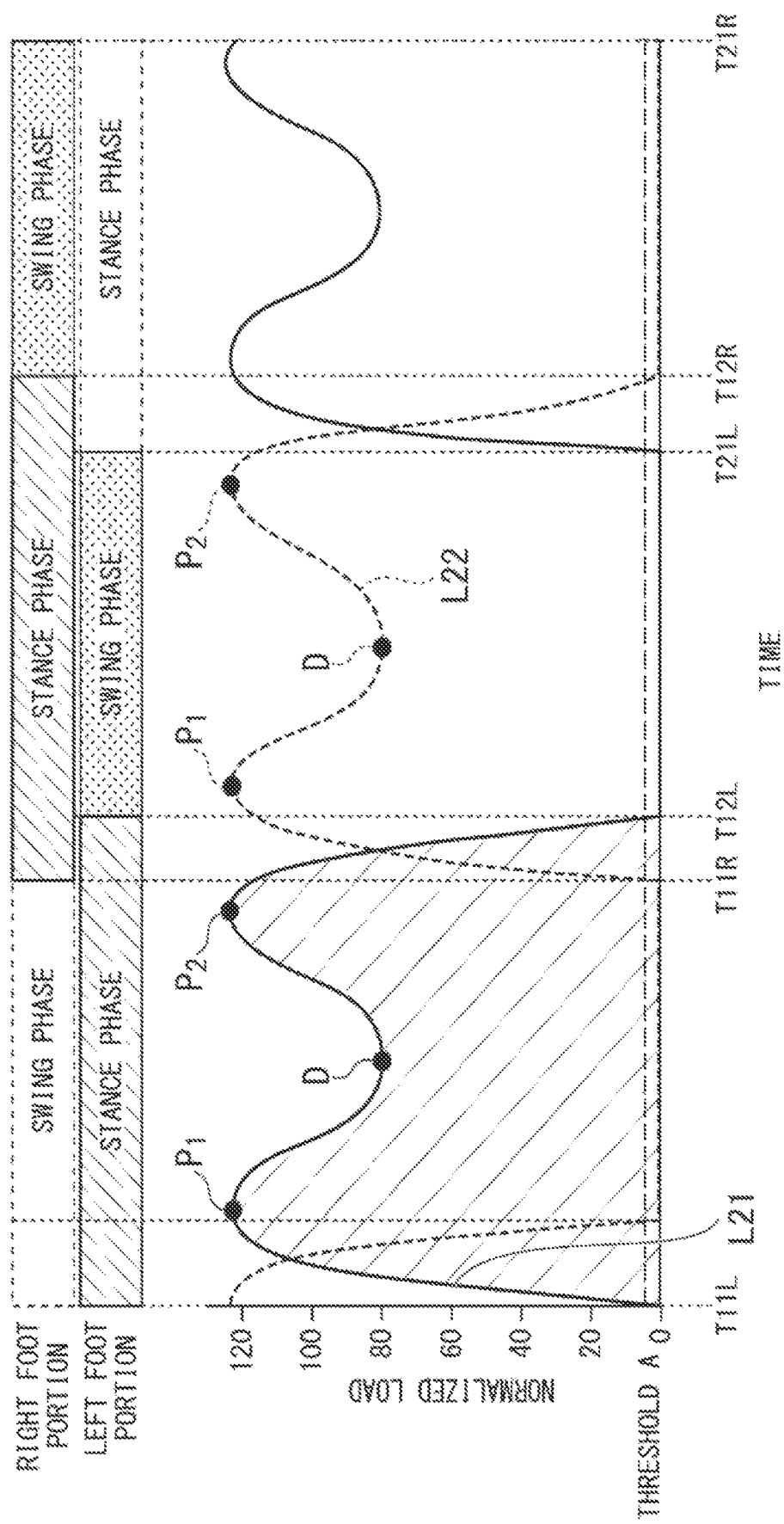
FIG. 6 is a diagram illustrating an example of measured values of foot pressures obtained by the sensor system according to the example embodiment.

FIG. 6 is a diagram illustrating an example of measured values of foot pressures obtained by the sensor system 100. The horizontal axis of FIG. 6 indicates times. The vertical axis of FIG. 6 indicates measured values of the foot pressures. The vertical axis of FIG. 6 indicates normalized values of foot pressures (normalized loads) with a reference value of the foot pressure as 100.

A line L21 indicates an example of measured values of the pressure of the left foot obtained by the left side sensor system 101. The line L21 indicates the values obtained by summing the foot pressure in the toes of the left foot by the left toe side sensor 111 and the foot pressure in the heel of the left foot by the left heel side sensor 121.

A line L22 indicates an example of measured values of the pressure of the right foot obtained by the right side sensor system 102. The line L22 indicates the values obtained by summing the foot pressure in the toes of the right foot by the right toe side sensor 112 and the foot pressure in the heel of the right foot by the right heel side sensor 122.

A threshold A is a threshold used for identifying the starting timing and the ending timing of the stance phase by the stance phase identification unit 293. The stance phase identification unit 293 compares the foot pressure with the threshold A and determines a timing at which the foot pressure changes from a value smaller than the threshold A to a value larger than the threshold A as the starting timing of the stance phase. Moreover, the stance phase identification unit 293 determines a timing at which the foot pressure changes from a value larger than the threshold A to a value smaller than the threshold A as the ending timing of the stance phase.

In the example of FIG. 6, the foot pressure of the left foot indicated by the line L21 changes from a value smaller than the threshold A to a value larger than the threshold A at a time T11L. Accordingly, the stance phase identification unit 293 determines the time T11L as the starting timing of the stance phase of the left foot.

Moreover, the foot pressure of the left foot indicated by the line L21 changes from a value larger than the threshold A to a value smaller than the threshold A at a time T12L. Accordingly, the stance phase identification unit 293 determines the time T12L as the ending timing of the stance phase of the left foot.

Furthermore, the foot pressure of the left foot indicated by the line L21 changes from a value smaller than the threshold A to a value larger than the threshold A at a time T21L. Accordingly, the stance phase identification unit 293 determines the time T21L as the starting timing of the stance phase of the left foot.

A period from the time T11L at which the stance phase of the left foot starts to the time T21L at which the stance phase of the left foot starts again corresponds to one walking cycle. One walking cycle determined on the basis of the left foot is also referred to as one walking cycle of the left foot.

Moreover, in the example of FIG. 6, the foot pressure of the right foot indicated by the line L22 changes from a value smaller than the threshold A to a value larger than the threshold A at a time T11R. Accordingly, the stance phase identification unit 293 determines the time T11R as the starting timing of the stance phase of the right foot.

Moreover, the foot pressure of the right foot indicated by the line L22 changes from a value larger than the threshold A to a value smaller than the threshold A at a time T12R. Accordingly, the stance phase identification unit 293 determines the time T12R as the ending timing of the stance phase of the right foot.

Furthermore, the foot pressure of the right foot indicated by the line L22 changes from a value smaller than the threshold A to a value larger than the threshold A at a time T21R. Accordingly, the stance phase identification unit 293 determines the time T21R as the starting timing of the stance phase of the right foot.

A period from the time T11R at which the stance phase of the right foot starts to the time T21R at which the stance phase of the right foot starts again corresponds to one walking cycle. One walking cycle determined on the basis of the right foot is also referred to as one walking cycle of the right foot.

In one walking cycle of the left foot from the time T11L to the time T21L and one walking cycle of the right foot from the time T11R to the time T21R, periods from the time T11R to the time T21L temporally overlap each other.

For example, the stance phase identification unit 293 may extract data for each walking cycle of the left foot from the measured data of the foot pressure of the left foot and may extract data for each walking cycle of the right foot from the measured data of the foot pressure of the right foot.

Moreover, the synchronization unit 292 may associate (synchronize) data for one walking cycle of the left foot with data for one walking cycle of the right foot starting during the one walking cycle of the left foot. For example, the synchronization unit 292 may associate the measured data of the foot pressure of the left foot during one walking cycle of the left foot from the time T11L to the time T21L with the measured data of the foot pressure of the right foot during one walking cycle of the right foot from the time T11R to the time T21R.

In this case, the risk estimation unit 294 may estimate a lower limb abnormality risk the basis of asymmetry between the associated stance phases during one walking cycle.

For example, one walking cycle of the left foot from the time T11L to the time T21L includes the stance phase from the time T11L to the time T12L. Moreover, one walking cycle of the right foot from the time T11R to the time T21R includes the stance phase from the time T11R to the time T12R. The risk estimation unit 294 may calculate the index value of asymmetry between the stance phase from the time T11L to the time T12L and the stance phase from the time T11R to the time T12R.

Various values can be used as the index value of asymmetry calculated by the risk estimation unit 294. For example, the risk estimation unit 294 may calculate any of the following as the index value of asymmetry by comparing the foot pressure of the left foot indicated by the line L21 and the foot pressure of the right foot indicated by the line L22 to each other.

(1) Difference Between Local Maximum Values of Foot Pressure Indicated by Point $P_1$ At a point $P_1$, when the stance phase starts, the heel has contacted the ground but the toes have not yet contacted the ground or have not sufficiently contacted the ground, and the foot on the opposite side is in the swing phase (takes off the ground) so that the weight is concentrated on the heel of one foot and a large measured value of the foot pressure is obtained by the heel side sensor 120.

(2) Difference Between Local Maximum Values of Foot Pressure Indicated by Point $P_2$ At a point $P_2$, when the stance phase ends, the heel floats, only the toes contacts the ground, and the foot on the opposite side has not yet touched the ground so that the weight is concentrated on the toes of one foot and a large measured value of the foot pressure is obtained by the toe side sensor 110.

(3) Difference Between Local Minimum Values of Foot Pressure Indicated by Point D At a point D, the foot sole of one foot (the shoe sole) entirely contacts the ground, and the weight is dispersed throughout the entire foot sole so that relatively small foot pressures are applied to the toe side sensor 110 and the heel side sensor 120.

(4) Difference Between Integral Values of Foot Pressure During One Walking Cycle In the example of FIG. 6, an integral value of the foot pressures during one walking cycle of the left foot is indicated as an area of a portion surrounded by the line L21 and the horizontal axis during the period from the time T11L to the time T21L. Moreover, an integral value of the foot pressures during one walking cycle of the right foot is indicated as an area of a portion surrounded by the line L22 and the horizontal axis during the period from the time T11R to the time T21R.

It should be noted that in the swing phase, the foot pressure becomes zero or approximately zero. Hence, the risk estimation unit 294 may calculate the integral value of the foot pressures for only the stance phase.

(5) Difference Between Average Values of Foot Pressures During Stance Phase

For example, the risk estimation unit 294 may perform sampling of the foot pressures during the stance phase in a predetermined sampling cycle and may calculate the average value. Alternatively, the risk estimation unit 294 may calculate the average value of the foot pressures by dividing the integral value of the foot pressures during the stance phase by a time.

(6) Value Obtained by Applying Predetermined Arithmetic Operation Such as the Four Basic Operations of Arithmetic to Values Obtained from (1) to (5) Described Above The risk estimation unit 294 may calculate a "ratio (proportion)" between the foot pressure of the left foot and the foot pressure of the right foot from (1) to (6) described above, in place of the "difference" between the foot pressure of the left foot and the foot pressure of the right foot.

In all the index values calculated from (1) to (5) described above, the larger the value, the greater asymmetry between the foot pressure of the left foot and the foot pressure of the right foot.

The risk estimation unit 294 may determine one of predetermined classifications of risk levels that corresponds to the calculated index value.

Figures 7, 8:
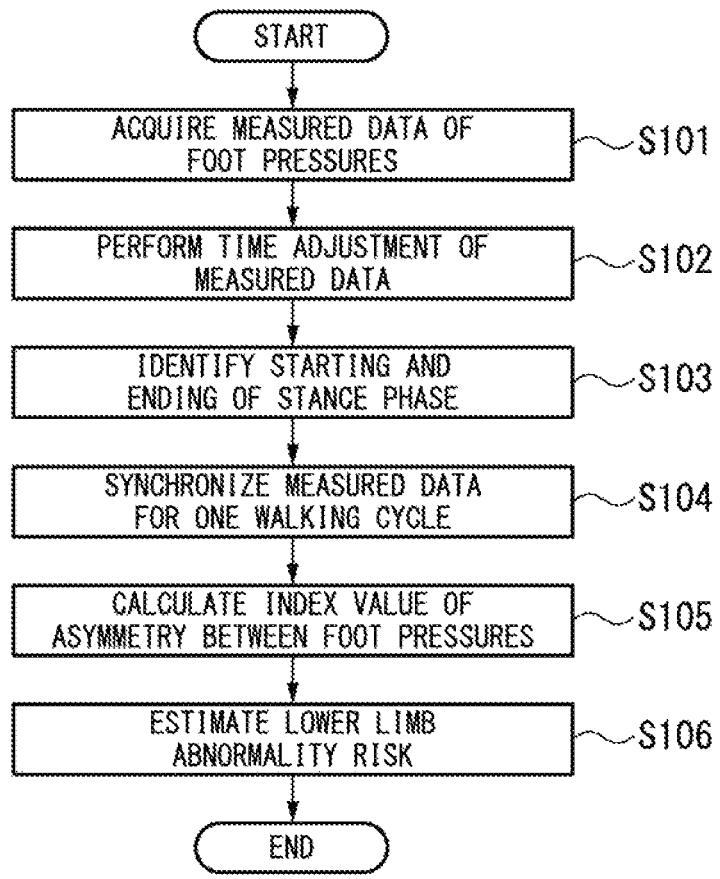
FIG. 7 is a diagram illustrating an example of risk level information stored in a storage unit according to the example embodiment.
FIG. 8 is a flowchart illustrating an example of a procedure of processing in which a risk estimation apparatus according to the example embodiment estimates a risk of abnormality of a lower limb (hereinafter referred to as "a lower limb abnormality risk".

FIG. 7 is a diagram illustrating an example of risk level information stored in the storage unit 280. The risk estimation unit 294 may estimate a lower limb abnormality risk using the risk level information.

In the example of FIG. 7, the risk level information is configured as data in a tabular format, and one row corresponds to one level of a lower limb abnormality risk. Each row of the risk level information includes a field of "asymmetry" and a field of "lower limb abnormality level".

The field of "lower limb abnormality level" shows a level of a lower limb abnormality risk. In the example of FIG. 7, "level 1", "level 2", "level 3", and so on are shown as the levels of a lower limb abnormality risk, and the larger the numerical value, the higher the risk.

The field of "asymmetry" shows a classification of the index value calculated by the risk estimation unit 294 with a minimum value and a maximum value. For example, if an index value x calculated by the risk estimation unit 294 satisfies $a \leq x < b$, the risk estimation unit 294 determines that the lower limb abnormality risk is in "level 1". If the index value x calculated by the risk estimation unit 294 satisfies $b \leq x < c$, the risk estimation unit 294 determines that the lower limb abnormality risk is in "level 2". If the index value x calculated by the risk estimation unit 294 satisfies $c \leq x < d$, the risk estimation unit 294 determines that the lower limb abnormality risk is in "level 3".

In this manner, the risk estimation unit 294 estimates a lower limb abnormality risk, and thus the subject person can be informed of the lower limb abnormality risk. When the lower limb abnormality risk is high, the subject person can seek for countermeasures such as improving the gait to reduce asymmetry between the foot pressure of the left foot and the foot pressure of the right foot.

It should be noted that the risk estimation unit 294 may estimate the level of a lower limb abnormality risk by a method other than referring to the risk level information, such as estimating the level of a lower limb abnormality risk through linear regression or machine learning.

Moreover, the risk estimation unit 294 may estimate the level of a lower limb abnormality risk using data for a plurality of walking cycles synchronized between the left foot and the right foot. For example, the risk estimation unit 294 may estimate the level of a lower limb abnormality risk using the average value of the foot pressures for a plurality of walking cycles.

Next, an operation of the risk estimation apparatus 200 will be described with reference to FIGS. 8 to 10.

FIG. 8 is a flowchart illustrating an example of a procedure of processing in which the risk estimation apparatus 200 estimates a lower limb abnormality risk.

In the processing of FIG. 8, the data acquisition unit 291 acquires the measured data of the foot pressure of the left foot and the measured data of the foot pressure of the right foot (step S101).

Moreover, the synchronization unit 292 performs time adjustment between the measured data of the foot pressure of the left foot and the measured data of the foot pressure of the right foot (step S102). For example, when the time (time stamp) attached to the measured data of the foot pressure of the left foot is later than the time attached to the measured data of the foot pressure of the right foot, the synchronization unit 292 may perform time adjustment advancing the time attached to the measured data of the foot pressure of the left foot by the time difference between the time attached to the measured data of the foot pressure of the right foot and the time attached to the measured data of the foot pressure of the left foot.

Next, the stance phase identification unit 293 identifies the starting timing of the stance phase and the ending timing of the stance phase for each of the measured data of the foot pressure of the left foot and the measured data of the foot pressure of the right foot (step S103). For example, as described with reference to FIG. 6, the stance phase identification unit 293 may identify the starting timing of the stance phase and the ending timing of the stance phase by comparing the measured value of the foot pressure with the threshold.

Through the processing of step S103, the measured data of the foot pressures is divided into pieces of data for each walking cycle. For example, the measured data of the foot pressures in the left foot during the period from the starting timing of the stance phase of the left foot to the starting timing of the next stance phase can be used as the measured data for one walking cycle of the left foot. The measured data of the foot pressures in the right foot during the period from the starting timing of the stance phase of the right foot to the starting timing of the next stance phase can be used as the measured data for one walking cycle of the right foot.

Next, the synchronization unit 292 synchronizes the measured data for one walking cycle of the left foot with the measured data for one walking cycle of the right foot (step S104). For example, as described with reference to FIG. 6, the synchronization unit 292 may synchronize (associate) the measured data for one walking cycle of the left foot with the measured data for one walking cycle of the right foot starting during the period of this walking cycle.

Next, the risk estimation unit 294 calculates the index value of asymmetry between the foot pressures using the synchronized measured data of the foot pressures of the left foot and the right foot (the measured data for one walking cycle of the foot pressures in the left foot and the measured data for one walking cycle of the foot pressures in the right foot that is associated with the measured data for one walking cycle of the foot pressures in the left foot) (step S105). As described above, various index values can be used as the index value of asymmetry between the foot pressures.

Further, the risk estimation unit 294 estimates a lower limb abnormality risk on the basis of the calculated index value (step S106). As described with reference to FIG. 7, the risk estimation unit 294 may estimate a lower limb abnormality risk using the risk level information. For example, the risk estimation unit 294 may cause the display unit 220 to display an estimated risk.

After step S106, the risk estimation apparatus 200 ends the processing of FIG. 8.

It should be noted that the processing procedure illustrated in FIG. 8 is an example of a procedure of processing performed by the risk estimation apparatus 200, and a procedure of processing performed by the risk estimation apparatus 200 is not limited thereto. For example, when the risk estimation apparatus 200 receives the measured data of the foot pressures from each of the left side sensor system 101 and the right side sensor system 102 in real time and a time stamp is attached by the risk estimation apparatus 200 side, time adjustment (step S102) of the measured data is not necessary. In the processing described with reference to FIGS. 9 and 10, a procedure of processing performed by the risk estimation apparatus 200 is also not limited thereto.

Figure 9:
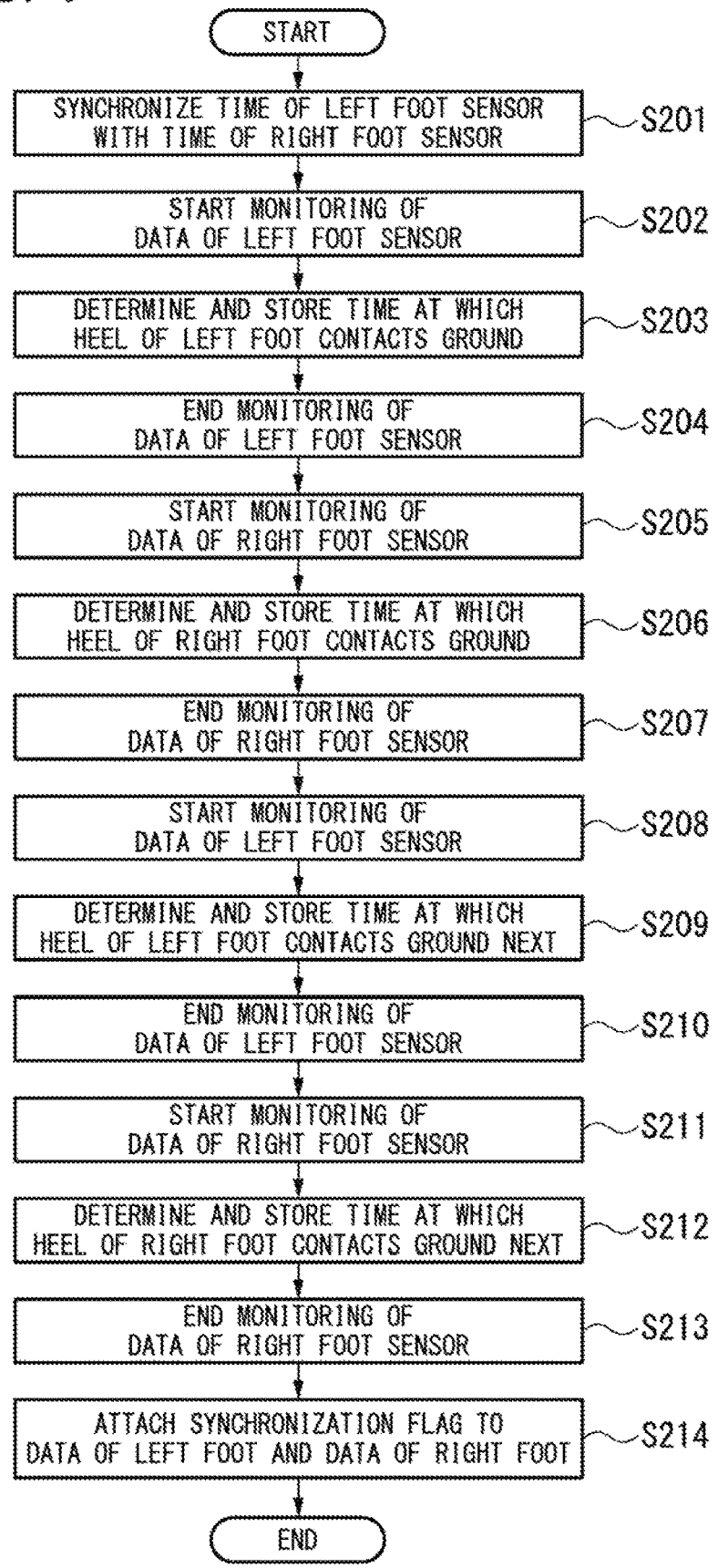
FIG. 9 is a flowchart illustrating an example of a procedure of processing in which the risk estimation apparatus according to the example embodiment synchronizes data of a left side sensor system with data of a right side sensor system.

FIG. 9 is a flowchart illustrating an example of a procedure of processing in which the risk estimation apparatus 200 synchronizes data of the left side sensor system 101 with data of the right side sensor system 102.

In the processing of FIG. 9, the synchronization unit 292 synchronizes the time of the left side sensor system 101 with the time of the right side sensor system 102 (step S201). For example, when a timepiece for a time stamp is built into each of the left side sensor system 101 and the right side sensor system 102, the synchronization unit 292 may adjust the time of the timepiece of the left side sensor system 101 and the time of the timepiece of the right side sensor system 102 to the time of the timepiece built into the synchronization unit 292 itself. Through the processing of step S201, the time attached to the measured data of the foot pressure of the left foot by the left side sensor system 101 is synchronized with the time attached to the measured data of the foot pressure of the right foot by the right side sensor system 102.

The processing of step S201 corresponds to an example of the processing of step S102 in FIG. 8.

Next, the stance phase identification unit 293 starts monitoring of the measured data of the foot pressures in the left foot using the left side sensor system 101 (step S202).

Further, the stance phase identification unit 293 determines the time at which the heel of the left foot contacts the ground and stores this time in the storage unit 280 as a starting time of the stance phase of the left foot (step S203). For example, as described with reference to FIG. 6, the stance phase identification unit 293 may detect the starting time of the stance phase (the time at which the heel contacts the ground) by comparing the measurement value of the foot pressure with the threshold.

The time at which the heel of the left foot contacts the ground, which is determined in step S203, will be expressed as a time T31L.

The stance phase identification unit 293, which has detected the starting time of the stance phase of the left foot in step S203, ends monitoring of the measured data of the foot pressure of the left foot (step S204) and starts monitoring of the measured data of the foot pressure of the right foot using the right side sensor system 102 (step S205).

Then, the stance phase identification unit 293 determines the time at which the heel of the right foot contacts the ground and stores the time in the storage unit 280 as a starting time of the stance phase of the right foot (step S206).

The time at which the heel of the right foot contacts the ground determined in step S206 will be expressed as a time T31R.

The stance phase identification unit 293, which has detected the starting time of the stance phase of the right foot in step S206, ends monitoring of the measured data of the foot pressure of the right foot (step S207) and starts monitoring of the measured data of the foot pressure of the left foot again using the left side sensor system 101 (step S208).

Then, the stance phase identification unit 293 determines the time at which the heel of the left foot contacts the ground and stores the time in the storage unit 280 as the starting time of the stance phase of the left foot next to the stance phase of the left foot detected in step S203 (step S209).

The time at which the heel of the left foot contacts the ground determined in step S209 will be expressed as a time T41L.

The stance phase identification unit 293, which has detected the starting time of the stance phase of the left foot in step S209, ends monitoring of the measured data of the foot pressure of the left foot (step S210) and starts monitoring of the measured data of the foot pressure of the right foot again using the right side sensor system 102 (step S211).

Then, the stance phase identification unit 293 determines the time at which the heel of the right foot contacts the ground and stores the time in the storage unit 280 as the starting time of the stance phase of the right foot next to the stance phase of the right foot detected in step S206 (step S212).

The time at which the heel of the right foot contacts the ground determined in step S212 will be expressed as a time T41R.

The stance phase identification unit 293, which has detected the starting time of the stance phase of the right foot in step S212, ends monitoring of the measured data of the foot pressure of the right foot (step S213).

The processing from step S202 to step S213 corresponds to an example of processing for identifying the starting timing of the stance phase in the processing of step S103 in FIG. 8.

Next, the synchronization unit 292 attaches a synchronization flag to the data for one walking cycle of the left foot and the data for one walking cycle of the right foot (step S214). A synchronization flag is a flag indicating that pieces of data are associated with each other through synchronization.

Specifically, the synchronization unit 292 associates the measured data of the foot pressures for one walking cycle of the left foot from the time T31L to the time T41L with the measured data of the foot pressures for one walking cycle of the right foot from the time T31R to the time T41R by applying a synchronization flag.

The processing of step S214 corresponds to an example of the processing of step S104 in FIG. 8.

After step S214, the risk estimation apparatus 200 ends the processing of FIG. 9.

Figure 10:
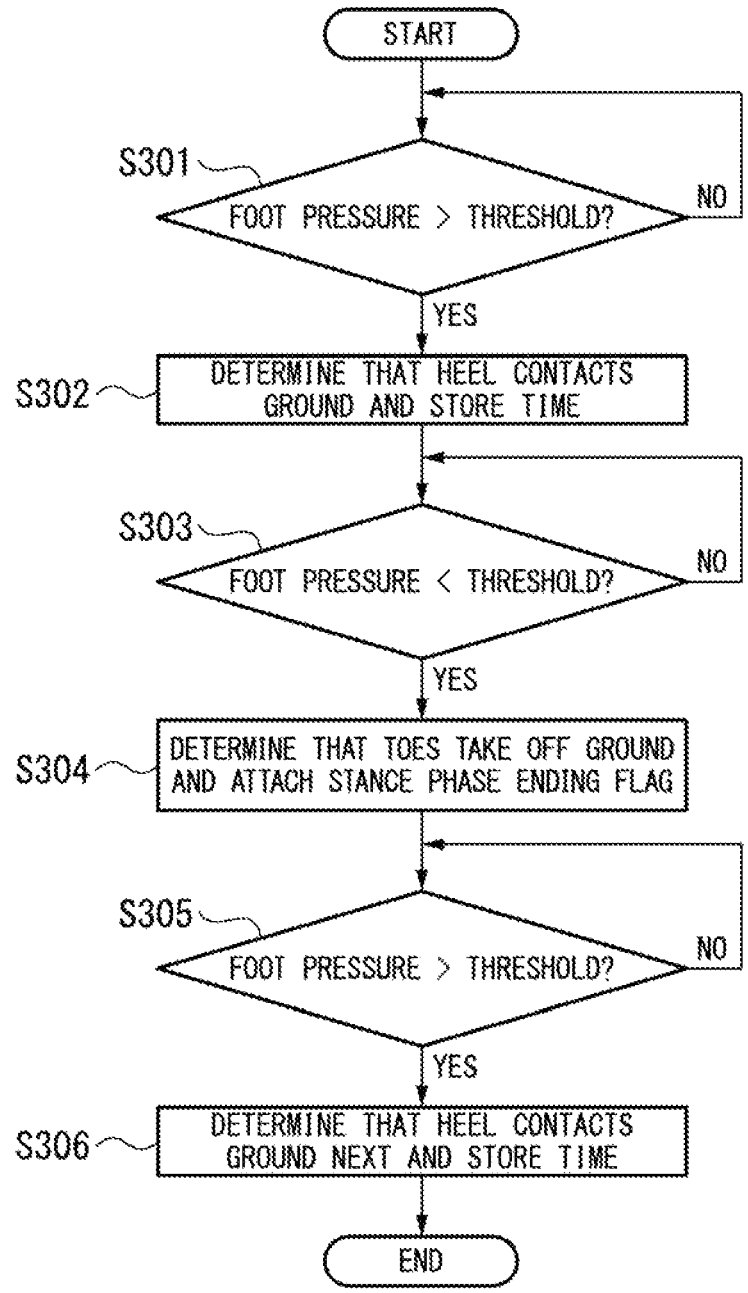
FIG. 10 is a flowchart illustrating an example of a procedure of processing in which the risk estimation apparatus according to the example embodiment determines the stance phases for data of the left side sensor system and data of the right side sensor system.

FIG. 10 is a flowchart illustrating an example of a procedure of processing in which the risk estimation apparatus 200 determines the stance phases for data of the left side sensor system 101 and data of the right side sensor system 102. The risk estimation apparatus 200 performs the processing of FIG. 10 for each of the measured data of the foot pressure of the left foot and the measured data of the foot pressure of the right foot.

The processing of FIG. 10 corresponds to an example of the processing of step S103 in FIG. 8.

In the processing of FIG. 10, the stance phase identification unit 293 refers to the measured data of the foot pressures in order of time and determines whether or not the foot pressure is larger than the threshold (step S301).

If the stance phase identification unit 293 determines that the foot pressure is equal to or smaller than the threshold (step S301: NO), the processing returns to step S301.

In contrast, if the stance phase identification unit 293 determines that the foot pressure is larger than the threshold (step S301: YES), the stance phase identification unit 293 determines that it is a timing at which the heel contacts the ground and stores this time in the storage unit 280 (step S302).

Next, the stance phase identification unit 293 further refers to the measured data of the foot pressures in order of time and determines whether or not the foot pressure is smaller than the threshold (step S303).

If the stance phase identification unit 293 determines that the foot pressure is equal to or larger than the threshold (step S303: NO), the processing returns to step S303.

In contrast, if the stance phase identification unit 293 determines that the foot pressure is smaller than the threshold (step S303: YES), the stance phase identification unit 293 determines that it is a timing at which the toes take off the ground and attaches a stance phase ending flag to the data at this time (step S304). Alternatively, the stance phase identification unit 293 may store this time in the storage unit 280 as the ending time of the stance phase.

Next, the stance phase identification unit 293 further refers to the measured data of the foot pressures in order of time and determines whether or not the foot pressure is larger than the threshold (step S305).

If the stance phase identification unit 293 determines that the foot pressure is equal to or smaller than the threshold (step S305: NO), the processing returns to step S305.

In contrast, if the stance phase identification unit 293 determines that the foot pressure is larger than the threshold (step S305: YES), the stance phase identification unit 293 determines that it is a timing at which the heel contacts the ground next to the timing at which the heel contacts the ground detected in step S302 and stores this time in the storage unit 280 (step S306).

After step S306, the risk estimation apparatus 200 ends the processing of FIG. 10.

Figure 11:
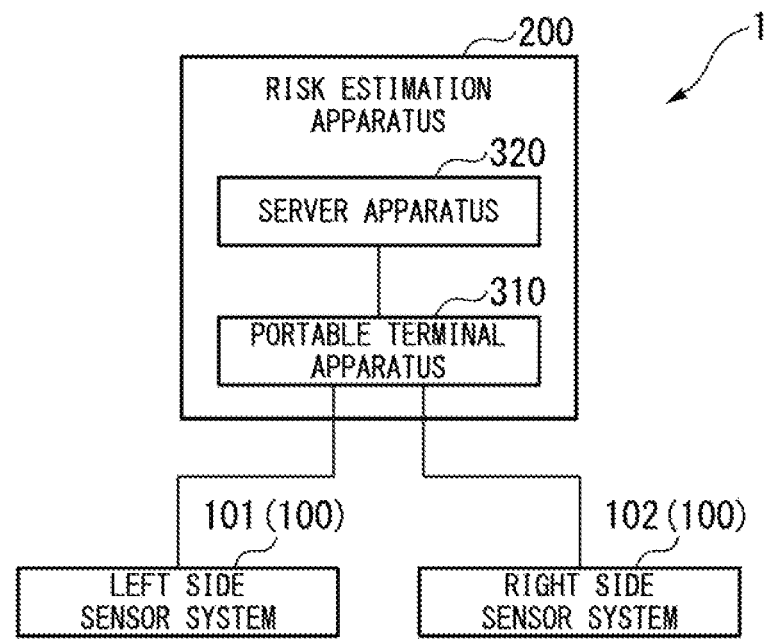
FIG. 11 is a diagram illustrating another example of a configuration of the risk estimation system according to the example embodiment.

FIG. 11 is a diagram illustrating another example of a configuration of the risk estimation system 1.

In the example of FIG. 11, the risk estimation apparatus 200 is configured to include a portable terminal apparatus 310 and a server apparatus 320.

For example, the portable terminal apparatus 310 is a device such as a smartphone which can communicate with each of the left side sensor system 101, the right side sensor system 102, and the server apparatus 320.

The server apparatus 320 is an apparatus that executes at least some of the functions of the risk estimation apparatus 200. The server apparatus 320 is configured using a computer such as a personal computer or a workstation.

In the configuration of FIG. 11, various kinds of allotment can be adopted as allotment of the functions of the risk estimation apparatus 200 between the portable terminal apparatus 310 and the server apparatus 320.

For example, the server apparatus 320 may execute the function of the risk estimation unit 294, and the portable terminal apparatus 310 may execute the other functions of the risk estimation apparatus 200. Alternatively, the portable terminal apparatus 310 may transfer data from the left side sensor system 101 and data from the right side sensor system 102 to the server apparatus 320 without any change, and the server apparatus 320 may execute each of the functions of the risk estimation apparatus 200.

As described above, the data acquisition unit 291 acquires the measured data of the foot pressures from each of the left side sensor system 101 and the right side sensor system 102. The stance phase identification unit 293 identifies the starting timing and the ending timing of the stance phase of each of the left foot and the right foot from the measured data of the foot pressures. The risk estimation unit 294 estimates a lower limb abnormality risk on the basis of asymmetry between the foot pressures of the left foot and the right foot during the stance phase.

In this manner, the risk estimation apparatus 200 can estimate a risk related to the feet other than a relationship between the feet and the shoes 810. The risk estimation apparatus 200 estimates a lower limb abnormality risk, and thus the subject person can be informed of the lower limb abnormality risk. When the lower limb abnormality risk is high, the subject person can seek for countermeasures such as improving the gait to reduce asymmetry between the foot pressure of the left foot and the foot pressure of the right foot.

Moreover, in the risk estimation system 1, sensors are provided in the shoes 810, and thus there is no need for the subject person to separately wear a wristband or the like, for example. In this regard, with the risk estimation system 1, it is possible to prevent the subject person from feeling inconvenience of attachment/detachment of the sensors or the like and the subject person from forgetting to wear the sensors.

Moreover, the subject person does not feel that he/she is wearing sensors, and thus it is expected that the subject person walks with a gait as in walking at a normal time. In this regard, the risk estimation system 1 can estimate a lower limb abnormality risk with high accuracy.

Moreover, the data acquisition unit 291 acquires the measured data of the foot pressures on the heel side and the toe side of each of the left foot and the right foot. The risk estimation unit 294 estimates a lower limb abnormality risk on the basis of asymmetry between the foot pressures on the heel side and the toe side of the left foot and the right foot during the stance phase.

In this manner, the risk estimation unit 294 estimates a lower limb abnormality risk using both the foot pressures on the heel side and the foot pressures on the toe side, and thus even when asymmetry occurs between the foot pressures on only one of the heel side and the toe side, a lower limb abnormality risk can be estimated by reflecting the asymmetry. In this regard, the risk estimation apparatus 200 can estimate a lower limb abnormality risk with high accuracy.

Moreover, the risk estimation unit 294 estimates a lower limb abnormality risk on the basis of asymmetry between the foot pressures of the left foot and the right foot during the stance phase of each of the left foot and the right foot in which parts of the measurement periods temporally overlap each other.

Assuming a case in which a measurement time of the measured data of the foot pressure of the left foot significantly differs from a measurement time of the measured data of the foot pressure of the right foot, it is conceivable that a walking mode at a time of measuring the foot pressure of the left foot differs from a walking mode at a time of measuring the foot pressure of the right foot, for example, a walking speed and a step length differ. Although the foot pressures of the left foot and the right foot are originally symmetrical, for example, the foot pressure of the left foot is substantially similar to the foot pressure of the right foot at the time of measuring the foot pressure of the left foot, there is a likelihood that the risk estimation apparatus 200 may erroneously determine that there is large asymmetry between the foot pressures in the left foot and the right foot because a measuring time of the foot pressure of the left foot differs from a measuring time of the foot pressure of the right foot and the walking modes differ.

In contrast, it is expected that the risk estimation unit 294 can determine asymmetry between the foot pressures with higher accuracy by determining asymmetry between the foot pressures using the foot pressures of the left foot and the right foot during the stance phase of each of the left foot and the right foot in which parts of the measurement periods temporally overlap each other (data of the foot pressures synchronized by the synchronization unit 292).

Figure 12:
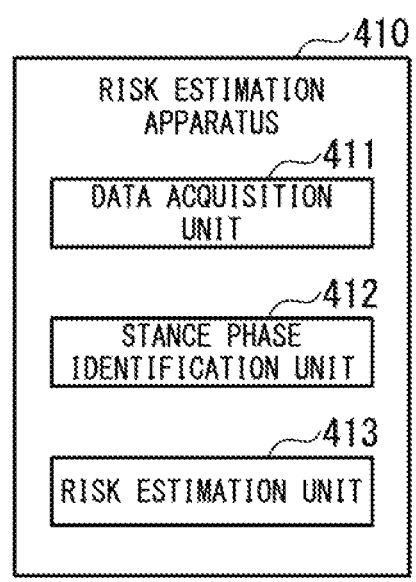
FIG. 12 is a diagram illustrating an example of a configuration of the risk estimation apparatus according to the example embodiment.

FIG. 12 is a diagram illustrating an example of a configuration of a risk estimation apparatus according to the example embodiment.

In the configuration illustrated in FIG. 12, a risk estimation apparatus 410 includes a data acquisition unit 411, a stance phase identification unit 412, and a risk estimation unit 413.

In the configuration, the data acquisition unit 411 acquires the measured data of the foot pressures obtained by sensors which are provided in shoes and measure the foot pressures of the left foot and the right foot. The stance phase identification unit 412 identifies the starting timing and the ending timing of the stance phase of each of the left foot and the right foot from the measured data of the foot pressures. The risk estimation unit 413 estimates a lower limb abnormality risk on the basis of asymmetry between the foot pressures of the left foot and the right foot during the stance phase.

In this manner, the risk estimation apparatus 410 can estimate a risk related to the feet other than a relationship between the feet and shoes. The risk estimation apparatus 410 estimates a lower limb abnormality risk and thus the subject person (the subject person for estimation of a lower limb abnormality risk) can be informed of the lower limb abnormality risk. When the lower limb abnormality risk is high, the subject person can seek for countermeasures such as improving the gait to reduce asymmetry between the foot pressure of the left foot and the foot pressure of the right foot.

Moreover, the risk estimation apparatuses 410 uses sensors provided in shoes and thus there is no need for the subject person to separately wear a wristband or the like, for example. In this regard, with the risk estimation apparatus 410, it is possible to prevent the subject person from feeling inconvenience of attachment/detachment of the sensors or the like and the subject person from forgetting to wear the sensors.

Moreover, the subject person does not feel that he/she is wearing sensors, and thus it is expected that the subject person walks with a gait as in walking at a normal time. In this regard, the risk estimation apparatus 410 can estimate a lower limb abnormality risk with high accuracy.

Figure 13:
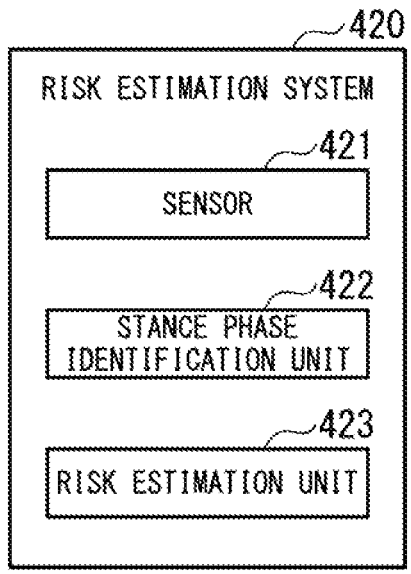
FIG. 13 is a diagram illustrating an example of a configuration of the risk estimation system according to the example embodiment.

FIG. 13 is a diagram illustrating an example of a configuration of a risk estimation system according to the example embodiment.

In the configuration illustrated in FIG. 13, a risk estimation system 420 includes sensors 421, a stance phase identification unit 422, and a risk estimation unit 423.

In the configuration, the sensors 421 are provided in shoes and measure the foot pressures of the left foot and the right foot. The stance phase identification unit 422 identifies the starting timing and the ending timing of the stance phase of each of the left foot and the right foot from the measured data of the foot pressures. The risk estimation unit 423 estimates a lower limb abnormality risk on the basis of asymmetry between the foot pressures of the left foot and the right foot during the stance phase.

In this manner, the risk estimation system 420 can estimate a risk related to the feet other than a relationship between the feet and shoes. The risk estimation system 420 estimates a lower limb abnormality risk, and thus the subject person (the subject person for estimation of a lower limb abnormality risk) can be informed of the lower limb abnormality risk. When the lower limb abnormality risk is high, the subject person can seek for countermeasures such as improving the gait to reduce asymmetry between the foot pressure of the left foot and the foot pressure of the right foot.

Moreover, the sensors 421 are provided in shoes, and thus there is no need for the subject person to separately wear a wristband or the like, for example. In this regard, with the risk estimation system 420, it is possible to prevent the subject person from feeling inconvenience of attachment/detachment of the sensors or the like and the subject person from forgetting to wear the sensors.

Moreover, the subject person does not feel that he/she is wearing sensors, and thus it is expected that the subject person walks with a gait as in walking at a normal time. In this regard, the risk estimation system 420 can estimate a lower limb abnormality risk with high accuracy.

Figure 14:
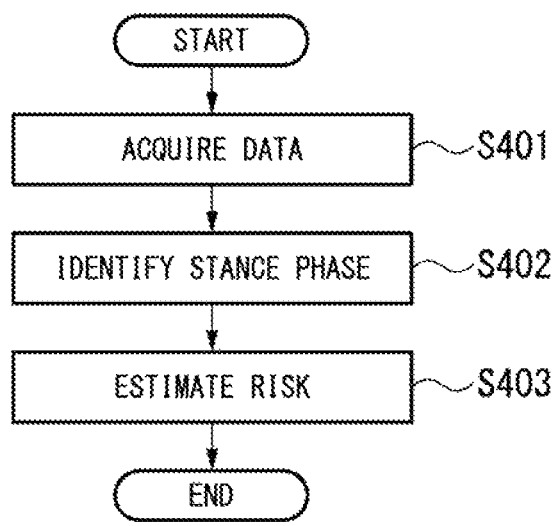
FIG. 14 is a flowchart illustrating an example of a procedure of processing in a risk estimation method of the risk estimation apparatus according to the example embodiment.

FIG. 14 is a flowchart illustrating an example of a procedure of processing in a risk estimation method of the risk estimation apparatus according to the example embodiment.

In the processing of FIG. 14, the risk estimation apparatus executes a step of acquiring measured data of foot pressures obtained by sensors that are provided in shoes and measure the foot pressures of the left foot and the right foot (step S401), a step of identifying a starting timing and an ending timing of a stance phase of each of the left foot and the right foot from the measured data of the foot pressures (step S402), and a step of estimating a lower limb abnormality risk on the basis of asymmetry between the foot pressures of the left foot and the right foot during the stance phase (step S403).

In this manner, with the processing of FIG. 14, a risk related to the feet other than a relationship between the feet and shoes can be estimated. The risk estimation apparatus estimates a lower limb abnormality risk using the processing of FIG. 14 and thus the subject person (the subject person for estimation of a lower limb abnormality risk) can be informed of the lower limb abnormality risk. When the lower limb abnormality risk is high, the subject person can seek for countermeasures such as improving the gait to reduce asymmetry between the foot pressures in the left foot and the foot pressure of the right foot.

Moreover, in the processing of FIG. 14, a risk estimation apparatus uses sensors provided in shoes, and thus there is no need for the subject person to separately wear a wristband or the like. In this regard, with the processing of FIG. 14, it is possible to prevent the subject person from feeling inconvenience of attachment/detachment of the sensors or the like and the subject person from forgetting to wear the sensors.

Moreover, the subject person does not feel that he/she is wearing sensors, and thus it is expected that the subject person walks with a gait as in walking at a normal time. In this regard, in FIG. 14, a lower limb abnormality risk can be estimated with high accuracy.

Figure 15:
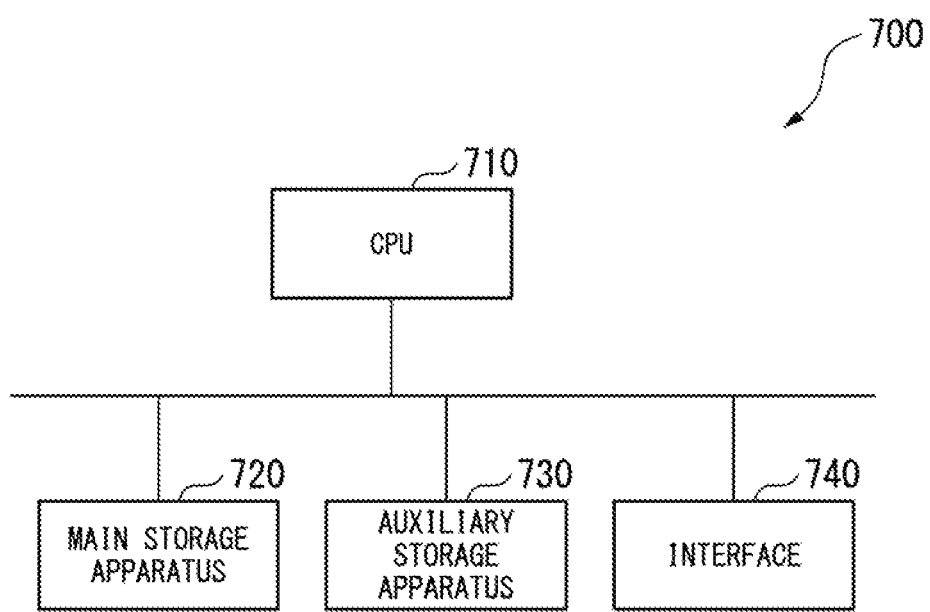
FIG. 15 is a schematic block diagram illustrating a configuration of a computer according to at least one of the example embodiments.

FIG. 15 is a schematic block diagram illustrating a configuration of a computer according to at least one of the example embodiments.

In the configuration illustrated in FIG. 15, a computer 700 includes a CPU 710, a main storage apparatus 720, an auxiliary storage apparatus 730, and an interface 740.

At least one of the risk estimation apparatus 200 and the risk estimation apparatus 410 may be implemented in the computer 700. In such a case, operation of each of the processing units described above is stored in the auxiliary storage apparatus 730 in a form of a program. The CPU 710 reads the program from the auxiliary storage apparatus 730, loads the program in the main storage apparatus 720, and executes the foregoing processing in accordance with the program. Moreover, the CPU 710 reserves storage areas corresponding to the storage units described above in the main storage apparatus 720 in accordance with the program. Communication between each of the apparatuses and other apparatuses is executed by having the interface 740 with a communication function and performing communication in accordance with control of the CPU 710.

When the risk estimation apparatus 200 is implemented in the computer 700, operation of the control unit 290 and each unit thereof are stored in the auxiliary storage apparatus 730 in a form of a program. The CPU 710 reads the program from the auxiliary storage apparatus 730, loads the program in the main storage apparatus 720, and executes the foregoing processing in accordance with the program.

Moreover, the CPU 710 reserves a storage area corresponding to the storage unit 280 in the main storage apparatus 720 in accordance with the program. Communication performed by the communication unit 210 is executed by having the interface 740 with a communication function and performing communication in accordance with control of the CPU 710. The function of the display unit 220 is executed by having the interface 740 with a display screen and displaying an image in the display screen in accordance with control of the CPU 710. The function of the operation input unit 230 is executed by having the interface 740 with an input device and receiving an operation of a user.

When the risk estimation apparatus 410 is implemented in the computer 700, operation of the data acquisition unit 411, the stance phase identification unit 412, and the risk estimation unit 413 is stored in the auxiliary storage apparatus 730 in a form of a program. The CPU 710 reads the program from the auxiliary storage apparatus 730, loads the program in the main storage apparatus 720, and executes the foregoing processing in accordance with the program.

It should be noted that the processing of each unit may be performed by recording a program for executing all or part of the processing performed by the risk estimation apparatus 200 and the risk estimation apparatus 410 in a computer readable recording medium and causing a computer system to read and execute the program recorded in this recording medium. It should be noted that a "computer system" here includes an operating system (OS) and hardware such as peripheral devices.

Moreover, a "computer readable recording medium" refers to a portable medium such as a flexible disk, a magneto-optical disc, a read only memory (ROM), or a compact disc read only memory (CD-ROM); or a storage apparatus such as a hard disk built into a computer system. Moreover, the foregoing program may be a program for realizing some of the functions described above, and may be a program capable of realizing the functions described above in combination with a program which has already been recorded in a computer system.

While the present invention has been particularly shown and described with reference to example embodiments thereof, the present invention is not limited to these example embodiments. It will be understood by those of ordinary skill in the art that various changes in form and details may be made therein without departing from the spirit and scope of the present invention as defined by the claims.

What is claimed is:

1. A risk estimation apparatus comprising:
   sensors measuring foot pressures of a left foot and a right foot, and provided in a right insole of shoes and a left insole of the shoes of a user;
   at least one memory storing instructions; and
   at least one processor configured to execute the instructions to:
      acquire, from the sensors, the measured data of the foot pressures of the left foot and the right foot, the measured data indicating a time variation of the foot pressures of the left foot and the right foot;
      attach a time stamp to the measured data of the foot pressures of the left foot and the right foot;
      identify a starting timing and an ending timing of a stance phase of each of the left foot and the right foot from the measured data of the foot pressures on the basis of the attached time stamp;
      estimate asymmetry between the foot pressures of the left foot and the right foot on the basis of a local maximum value and a local minimum value of the measured data of the time variation of the foot pressures collected during a corresponding stance phase; and
      estimate, by using a machine learned model, a risk of abnormality of a lower limb on the basis of the asymmetry between the foot pressures of the left foot and the right foot during the stance phase of each of the left foot and the right foot in which parts of measurement periods temporally overlap each other,
   wherein a risk level is used for making a decision related to improving a gait to reduce asymmetry between the foot pressures of the left foot and the right foot.

2. The risk estimation apparatus according to claim 1, wherein the at least one processor is further configured to execute the instructions to:
   acquire the measured data of the foot pressures on a heel side and a toe side of each of the left foot and the right foot; and
   estimate the risk of the abnormality of the lower limb on the basis of the asymmetry between the foot pressures on the heel side and the toe side of the left foot and the right foot during the stance phase.

3. The risk estimation apparatus according to claim 1, wherein two sensors are provided in the left shoe and two sensors are provided in the right shoe.

4. The risk estimation apparatus according to claim 3, wherein one sensor of the two sensors provided in the left shoe is installed on a toe side of the left shoe, and another sensor of the two sensors provided in the left shoe is installed on a heel side of the left shoe, and
   wherein one sensor of the two sensors provided in the right shoe is installed on a toe side of the right shoe, and another sensor of the two sensors provided in the right shoe is installed on a heel side of the right shoe.

5. The risk estimation apparatus according to claim 1, wherein the sensors provided in the left shoe and the right shoe are installed in a bilaterally symmetrical manner with respect to each other.

6. A risk estimation method performed by a computer and comprising:
   acquiring, from sensors measuring foot pressures of a left foot and a right foot, and provided in a right insole of shoes and a left insole of the shoes of a user, the measured data of the foot pressures of the left foot and the right foot, the measured data indicating a time variation of the foot pressures of the left foot and the right foot;
   attaching a time stamp to the measured data of the foot pressures of the left foot and the right foot;
   identifying a starting timing and an ending timing of a stance phase of each of the left foot and the right foot from the measured data of the foot pressures on the basis of the attached time stamp;
   estimating asymmetry between the foot pressures of the left foot and the right foot on the basis of a local maximum value and a local minimum value of the measured data of the time variation of the foot pressures collected during a corresponding stance phase; and
   estimating, by using a machine learned model, a risk of the abnormality of a lower limb on the basis of the asymmetry between the foot pressures of the left foot and the right foot during the stance phase of each of the left foot and the right foot in which parts of measurement periods temporally overlap each other,
   wherein a risk level is used for making a decision related to improving a gait to reduce asymmetry between the foot pressures of the left foot and the right foot.

7. The risk estimation method according to claim 6, further comprising:
   acquiring the measured data of the foot pressures on a heel side and a toe side of each of the left foot and the right foot; and
   estimating the risk of the abnormality of the lower limb on the basis of the asymmetry between the foot pressures on the heel side and the toe side of the left foot and the right foot during the stance phase.

8. The risk estimation method according to claim 6, wherein two sensors are provided in the left shoe and two sensors are provided in the right shoe.

9. The risk estimation method according to claim 8, wherein one sensor of the two sensors provided in the left shoe is installed on a toe side of the left shoe, and another sensor of the two sensors provided in the left shoe is installed on a heel side of the left shoe, and
   wherein one sensor of the two sensors provided in the right shoe is installed on a toe side of the right shoe, and another sensor of the two sensors provided in the right shoe is installed on a heel side of the right shoe.

10. The risk estimation method according to claim 6, wherein the sensors provided in the left shoe and the right shoe are installed in a bilaterally symmetrical manner with respect to each other.

11. A non-transitory storage medium storing a program executable by a computer to perform a risk estimation method comprising:
    acquiring, from sensors measuring foot pressures of a left foot and a right foot, and provided in a right insole of shoes and a left insole of the shoes of a user, the measured data of the foot pressures of the left foot and the right foot, the measured data indicating a time variation of the foot pressures of the left foot and the right foot;

attaching a time stamp to the measured data of the foot pressures of the left foot and the right foot;

identifying a starting timing and an ending timing of a stance phase of each of the left foot and the right foot from the measured data of the foot pressures on the basis of the attached time stamp;

estimating asymmetry between the foot pressures of the left foot and the right foot on the basis of a local maximum value and a local minimum value of the measured data of the time variation of the foot pressures collected during a corresponding stance phase; and estimating, by using a machine learned model, a risk of the abnormality of a lower limb on the basis of the asymmetry between the foot pressures of the left foot and the right foot during the stance phase of each of the left foot and the right foot in which parts of measurement periods temporally overlap each other, wherein a risk level is used for making a decision related to improving a gait to reduce asymmetry between the foot pressures of the left foot and the right foot.

12. The non-transitory storage medium according to claim 11, wherein the risk estimation method further comprises:
    acquiring the measured data of the foot pressures on a heel side and a toe side of each of the left foot and the right foot; and
    estimating the risk of the abnormality of the lower limb on the basis of the asymmetry between the foot pressures on the heel side and the toe side of the left foot and the right foot during the stance phase.

13. The non-transitory storage medium according to claim 11, wherein two sensors are provided in the left shoe and two sensors are provided in the right shoe.

14. The non-transitory storage medium according to claim 13, wherein one sensor of the two sensors provided in the left shoe is installed on a toe side of the left shoe, and another sensor of the two sensors provided in the left shoe is installed on a heel side of the left shoe, and
    wherein one sensor of the two sensors provided in the right shoe is installed on a toe side of the right shoe, and another sensor of the two sensors provided in the right shoe is installed on a heel side of the right shoe.

15. The non-transitory storage medium according to claim 11, wherein the sensors provided in the left shoe and the right shoe are installed in a bilaterally symmetrical manner with respect to each other.

* * * * *